US010537392B2

(12) United States Patent
Millahn et al.

(10) Patent No.: US 10,537,392 B2
(45) Date of Patent: Jan. 21, 2020

(54) METHOD FOR ENABLING MEDICAL NAVIGATION WITH MINIMISED INVASIVENESS

(75) Inventors: Manuel Millahn, Munich (DE); Bert Bracke, Vaterstetten (DE); Christian Brack, Neusäss (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 13/582,077

(22) PCT Filed: Mar. 3, 2010

(86) PCT No.: PCT/EP2010/052679
§ 371 (c)(1),
(2), (4) Date: Aug. 31, 2012

(87) PCT Pub. No.: WO2011/107147
PCT Pub. Date: Sep. 9, 2011

(65) Prior Publication Data
US 2012/0330135 A1    Dec. 27, 2012

(51) Int. Cl.
*A61B 34/20* (2016.01)
*A61B 34/10* (2016.01)
*A61B 90/00* (2016.01)
*A61B 17/17* (2006.01)
*A61B 17/15* (2006.01)

(52) U.S. Cl.
CPC .............. *A61B 34/20* (2016.02); *A61B 17/15* (2013.01); *A61B 17/1764* (2013.01); *A61B 2034/107* (2016.02); *A61B 2034/2068* (2016.02); *A61B 2034/2074* (2016.02); *A61B 2090/363* (2016.02)

(58) Field of Classification Search
CPC ................ A61B 17/15; A61B 17/1764; A61B 2034/107; A61B 2034/2068; A61B 2034/2074; A61B 2090/363; A61B 34/20
USPC ....................................................... 600/424
See application file for complete search history.

(56) References Cited

U.S. PATENT DOCUMENTS 5,682,886 A * 11/1997 Delp et al. .................... 600/407
6,560,354 B1 * 5/2003 Maurer et al. ................ 382/131
(Continued)

FOREIGN PATENT DOCUMENTS

EP    2 135 575    12/2009

OTHER PUBLICATIONS

International Search Report for International Application No. PCT/EP2010/052679 dated Nov. 12, 2010.

*Primary Examiner* — Amelie R Gillman
(74) *Attorney, Agent, or Firm* — Pepper Hamilton LLP

(57) ABSTRACT

A method for providing positional relationship data, which represent the position of a marker device relative to a bone which it is affixed to, to a medical navigation system, comprising the steps of: a) receiving bone registration data which represent locations of points on the surface of the bone; b) calculating, from the bone registration data, the current relative position between the bone and a medical instrument which bears the marker device; c) determining an offset between the current relative position and a desired relative position; d) outputting indication information which is based on the calculated offset; e) receiving bone re-registration data which represent locations of points on the surface of the bone; and f) calculating the positional relationship data from the bone re-registration data.

21 Claims, 4 Drawing Sheets

(56) References Cited

U.S. PATENT DOCUMENTS

| | | | |
|---|---|---|---|
| 2002/0133175 A1* | 9/2002 | Carson | A61B 90/10 606/130 |
| 2005/0190380 A1* | 9/2005 | Plassky | A61B 17/15 356/614 |
| 2005/0203531 A1 | 9/2005 | Lakin et al. | |
| 2005/0245808 A1* | 11/2005 | Carson | A61B 34/20 600/407 |
| 2006/0015018 A1* | 1/2006 | Jutras | A61B 34/20 600/301 |
| 2006/0110071 A1* | 5/2006 | Ong et al. | 382/294 |
| 2006/0122491 A1* | 6/2006 | Murray | A61B 17/157 600/414 |
| 2006/0155291 A1* | 7/2006 | Farrar et al. | 606/87 |
| 2006/0173291 A1* | 8/2006 | Glossop | A61B 90/96 600/424 |
| 2006/0195048 A1 | 8/2006 | Leitner et al. | |
| 2006/0217733 A1* | 9/2006 | Plassky et al. | 606/87 |
| 2006/0241405 A1* | 10/2006 | Leitner | A61B 5/103 600/426 |
| 2006/0285641 A1* | 12/2006 | Scherch | A61B 5/064 378/65 |
| 2007/0055232 A1* | 3/2007 | Colquhoun | A61B 90/39 606/54 |
| 2007/0249967 A1* | 10/2007 | Buly et al. | 600/595 |
| 2007/0299334 A1* | 12/2007 | Vilsmeier | 600/414 |
| 2008/0039716 A1* | 2/2008 | Tuma | A61B 90/36 600/424 |
| 2009/0292200 A1* | 11/2009 | Kindlein et al. | 600/425 |

* cited by examiner

METHOD FOR ENABLING MEDICAL NAVIGATION WITH MINIMISED INVASIVENESS

This application is a national phase of International Application No. PCT/EP2010/052679 filed Mar. 3, 2010 and published in the English language.

The present invention relates to a method for providing positional relationship data, which represent the position of a marker device relative to a bone which it is affixed to, to a medical navigation system, and relates to a medical navigation system and a method for performing computer-assisted surgery.

BACKGROUND

In recent years, computer-assisted surgery using medical navigation systems (also referred to as surgical navigation systems) has become widely popular. Computer-assisted surgery increases the efficiency and accuracy of surgical interventions and enables an operation to be documented by detecting and tracking the positions of body structures and medical instruments and by deriving information for the surgeon from these data.

In order to enable a medical instrument or a body structure to be handled by the medical navigation system, it is necessary to provide the instrument or structure with a marker device which can be detected by the medical navigation system. For a body structure in particular, this means that the marker device must be rigidly affixed to the structure. This often causes additional damage to the body structure, the negative effects of which have to be traded off against the benefits of faster, more efficient or more accurate surgery. If the body structure is for example a bone, the marker device is usually affixed to the bone using a pin, a bolt or a Schanz screw, thus resulting in an additional hole imposed on the bone.

BRIEF SUMMARY

Using the method and the medical navigation system according to the present invention, it is possible to omit the use of a dedicated marker device which is rigidly affixed to the body structure, in particular a bone, by using a marker device which is affixed to a medical instrument which is in turn rigidly affixed to the body structure, for navigation.

The method for providing positional relationship data, which represent the position of a marker device relative to a bone which it is affixed to, to a medical navigation system according to the present invention comprises the steps of:
a) receiving bone registration data which represent locations of points on the surface of the bone;
b) calculating, from the bone registration data, the current relative position between the bone and a medical instrument which bears the marker device;
c) determining an offset between the current relative position and a desired relative position;
d) outputting indication information which is based on the calculated offset;
e) receiving bone re-registration data which represent locations of points on the surface of the bone; and
f) calculating the positional relationship data from the bone re-registration data.

In this document, the term "position" of an object encompasses both the location and the alignment or orientation of the object, and the term "location" means the point in space, specified for example using spatial co-ordinates, at which the object is located and defined in up to three translational dimensions. The term "alignment" or "orientation" means the rotational alignment of an object in space and is specified in up to three rotational dimensions.

A marker device can for example be a reference star or a pointer or one or more (individual) markers in a predetermined spatial relationship. A marker device comprises one, two, three or more markers in a predetermined spatial relationship. This predetermined spatial relationship is in particular known to the navigation system and for example stored in a computer of the navigation system.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In surgical navigation, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

Step a) of the method according to the present invention involves receiving bone registration data which are provided. The bone registration data represent locations of points on the surface of the bone and therefore contain sampling points which could be used for morphing a generic model of the bone in order to reproduce the actual bone. Preferably, the bone registration data contain enough points, for example 5 to 50 points, to enable accurate morphing or matching. Preferably, the points whose locations are represented by the bone registration data are landmarks.

A landmark is a defined position of an anatomical characteristic of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure or only a point or part of it. A landmark can for example also lie on the anatomical structure which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement between two body parts, such as the rotational centre of the femur when moved relative to the acetabulum.

Preferably, the points on the surface of the bone are sampled using a pointer. A pointer is a rod comprising one or more—advantageously, two—markers fastened to it, wherein the pointer can be used to measure off individual co-ordinates, in particular spatial co-ordinates (i.e. three-dimensional co-ordinates), on a part of the body such as a bone, wherein a user guides the pointer (in particular, a part of the pointer which has a defined and advantageously fixed location with respect to the at least one marker which is attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (in particular, the tip of the pointer) is in particular known. The surgical navigation system then enables the location (of the three-dimensional co-ordinates) to be assigned to a predetermined body structure, wherein the assignment can be made automatically or by user intervention.

In Step b), the current relative position between the bone and a medical instrument which bears the marker device is calculated from the bone registration data. In this step, a positional relationship between the structure of the bone and the marker device on the medical instrument is established. The medical instrument is rigidly affixed to the bone. Since the marker device is rigidly affixed to the medical instrument, it is also rigidly affixed with respect to the bone. In a preferred example, the medical instrument is a cutting block comprising a cutting slot for sawing a part of the bone off, for example in order to provide an artificial joint.

In Step c), an offset between the current relative position calculated in Step b) and a desired relative position is determined. The determination is preferably a calculation, but can also be a measurement. The desired relative position is a target position at which the medical instrument is to be positioned relative to the bone, for example for sawing off a part of the bone, A relative position is preferably represented by relative position data. The offset is indicative of the accuracy with which the medical instrument is positioned.

In Step d), indication information which is based on the determined offset is outputted. The indication information can be an indication information signal or indication information data. For example, the indication information can be optical information showing absolute values of the offset in up to three rotational and/or up to three translational dimensions. Other examples of indication information include optical, acoustic or tactile signals which indicate that the offset is below or above a threshold. Whether the offset is above or below the threshold can be determined on the basis of one or more rotational and/or translational components of the offset. For example, the largest component of the offset can be compared to a threshold, or the average of one or more components of the offset can be compared to the threshold. In particular, Steps a) to d) are repeated until the offset is below the threshold.

In Step e) of the method, bone re-registration data are received. Like the bone registration data, the bone re-registration data represent locations of points on the surface of the bone. The bone re-registration data therefore contain information about the position of the bone. The positional relationship, which represents the position of the marker device relative to the bone, is calculated from the bone re-registration data in Step f). In this step, the positional relationship between the bone and the medical instrument, and therefore the marker device, is re-established. The positional relationship data can then be used by the medical navigation system to determine or track the position of the bone by determining or tracking the position of the marker device. This means that navigation can be performed without having to damage the bone by affixing a dedicated marker device.

If the marker device is moved, for example together with the medical instrument, relative to the bone between Steps d) and e), the established positional relationship between the marker device and the bone is lost. This means that the position of the bone cannot be deduced from the position of the marker device. In order to prevent an inaccurate navigation, the indication information preferably contains the information that the established positional relationship between the bone and the instrument is lost when the instrument is moved relative to the bone.

In order to perform the calculation in Step f), it is necessary to also know marker device position data which represent the position of the marker device, because the positional relationship data represent a relative position between the marker device and the bone.

There are different ways of calculating the current relative position between the bone and the medical instrument and/or the positional relationship data. In one embodiment, the bone registration data and/or the bone re-registration data are specified in a co-ordinate system which is defined relative to the marker device. This means that the co-ordinate system is linked to the marker device, and the bone registration data or bone re-registration data, respectively, represent the locations of the points on the surface of the bone relative to the marker device.

In an alternative embodiment, marker device position data which represent the position of the marker device, and the bone registration data and/or bone re-registration data, are specified in an external co-ordinate system. The external co-ordinate system can for example be linked to a room or to the medical navigation system, in particular to a marker detection device of the medical navigation system.

If Steps e) and f) are omitted, the remaining Steps a) to d) are then a method for providing indication information which represents an offset between a current relative position between a bone and a medical instrument and a desired relative position. The advantage of this method is the same as the advantage of the method for providing positional relationship data, i.e. that of providing the data or information without having to rigidly affix a dedicated marker device to the bone, thereby damaging the bone.

To briefly summarise the method: bone registration data are received in order to calculate a positional relationship between the bone and the medical instrument (or a part of the medical instrument), and an offset between the current relative position between the bone and the medical instrument and a desired relative position is then calculated. Information which is based on this offset is then provided to a surgeon who can then re-adjust the medical instrument.

When the medical instrument is re-adjusted, the previously calculated positional relationship is lost. In order to re-establish this positional relationship for subsequent use in a medical navigation system, bone re-registration data are received and used to calculate the positional relationship between the bone and the marker device which is affixed to the medical instrument.

In a preferred embodiment, the bone re-registration data are a reduced set of data as compared to the bone registration data, i.e. the bone re-registration data contain the locations of fewer points on the surface of the bone than the bone registration data. This is possible because the bone re-registration data are only used to determine the position of the bone and not necessarily to obtain the shape of the bone.

In one example, the bone re-registration data received in Step e) are augmented by at least parts of the bone registration data received in Step a). Since the relative locations between points on the surface of the bone do not change, it is sufficient to receive the locations of only a few points, for example three points, on the surface of the bone as sample points. The locations of the missing points in the bone re-registration data can then be calculated from the distance between the points in the bone registration data which correspond to the missing points and the points in the bone registration data which correspond to the sample points.

In another example, the bone registration data received in Step a) are used in Step f) to calculate the positional relationship data. For example, the bone re-registration data only contain the locations of a limited number of points on the surface of the bone, and the bone registration data are transformed, i.e. subjected to co-ordinate transformation, such that the points in the bone re-registration data match corresponding points in the bone registration data. The transformation in particular constitutes a rotational and/or rotational shift in the bone registration data. The transformed bone registration data then represent the bone in its current position.

In another preferred embodiment, a step of receiving the number of degrees of freedom of movement of the bone is added between Steps d) and e) of the method described above. Depending on the number of degrees of freedom, a different number of points whose locations are represented by the bone re-registration data is sufficient to calculate the current position of the bone. The number of degrees of freedom can for example be received from a storage device such as a memory or from an input device such as a keyboard or a touch screen. Preferably, the number of points is equal to or larger than the number of degrees of freedom. In particular, if the movement of the bone is restricted to one degree of freedom, the location of one point is sufficient, while the locations of two points are sufficient for two degrees of freedom.

An additional step of outputting the number and/or identification of points on the surface of the bone to be registered can optionally be performed. The source of the bone re-registration data then knows how many and/or which points have to be contained in the bone re-registration data in order to reliably calculate the positional relationship data.

The method for providing positional relationship data, which represent the position of a marker device relative to a bone which it is affixed to, to a medical navigation system as explained above does not comprise the steps of ascertaining or measuring the locations of the points on the surface of the bone as far as surgical measures, such as incisions or invasive interventions, are required or involved. These locations, which are represented by the bone registration data and/or the bone re-registration data, are pre-acquired and then provided or acquired in a way which does not require professional medical care and expertise to be carried out. Re-adjusting the medical instrument is also either not part of the method according to the present invention or can be carried out in a way which does not require professional medical expertise. Alternatively, re-adjustment can even occur unintentionally. In general, how and why the positional relationship between the bone and the marker device is lost between the steps of receiving the bone registration data and receiving the bone re-registration data is irrelevant to and therefore not necessarily part of the present invention.

The present invention also relates to a computer program which, when executed on a processor, causes the processor to execute the method explained above. The invention also relates to a computer-readable medium comprising such a computer program and to a computer on which the computer program is running or into the memory of which the computer program is loaded.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

Another aspect of the present invention is a medical navigation system for computer-assisted surgery, comprising the computer described above, a device for providing the bone registration data and/or the bone re-registration data and an output device for outputting the indication information. The device for providing the bone registration data and/or the bone re-registration data is preferably a marker detection device which is capable of detecting the position or location of a marker device, such as a marker device of a pointer.

The present invention also relates to a method for preparing computer-assisted surgery, comprising the followings steps:
- aa) determining bone registration data which represent locations of points on the surface of a bone;
- ab) calculating, from the bone registration data, the current relative position between the bone and a medical instrument which bears a marker device;
- ac) determining an offset between the current relative position and a desired relative position;
- ad) adjusting the medical instrument on the basis of the calculated offset;
- ae) determining bone re-registration data which represent locations of points on the surface of the bone; and
- af) calculating the relative position between the bone and the marker device from the bone re-registration data, and providing said relative position for computer-assisted surgery.

Preferably, the bone registration data are determined in Step aa) using a pointer which comprises a tip and a marker device. The tip of the pointer is placed on the point to be sampled, and the location of the point is determined from the position of the marker on the pointer and the known relative position between the tip and the marker on the pointer.

Steps ab) and ac) correspond to Steps b) and c) of the method described above. The determined offset, or mismatch, is indicative of whether and how the current relative position of the medical instrument differs from the desired relative position. In Step ad), the medical instrument is adjusted on the basis of the calculated offset. If the medical instrument is a simple cutting block which is connected to the bone via screws, bolts or pins which are fixed into the bone, then the adjusting step can involve replacing the cutting block with another cutting block, such that the cutting slot of the new cutting block is in the desired position. If the medical instrument is an adjustable cutting block, then the cutting block can be adjusted, for example using setting screws, such that the cutting slot of the cutting block is in the desired position. In a preferred embodiment, the target positions of the setting screws in which the cutting slot is in its desired position are calculated from the offset and displayed to the person adjusting the medical instrument.

In Steps ae) and af), bone re-registration data are determined and used to calculate the relative position between the bone and the marker device. The relative position defines a positional relationship between the bone and the marker, such that computer-assisted surgery can be performed on the basis of the relative position by determining the position of the bone from the position of the marker device. In the next step carried out after the method according to the present invention, the computer-assisted surgery is performed.

It is possible to omit non-essential features from the embodiments and examples described above and to combine one or more or all of the features of two or more embodiments or examples, to form a new embodiment or example.

BRIEF DESCRIPTION OF THE DRAWINGS

The present invention shall now be explained in more detail on the basis of an example embodiment which is described with reference to the appended figures. The figures show.

DETAILED DESCRIPTION

Figure 1:
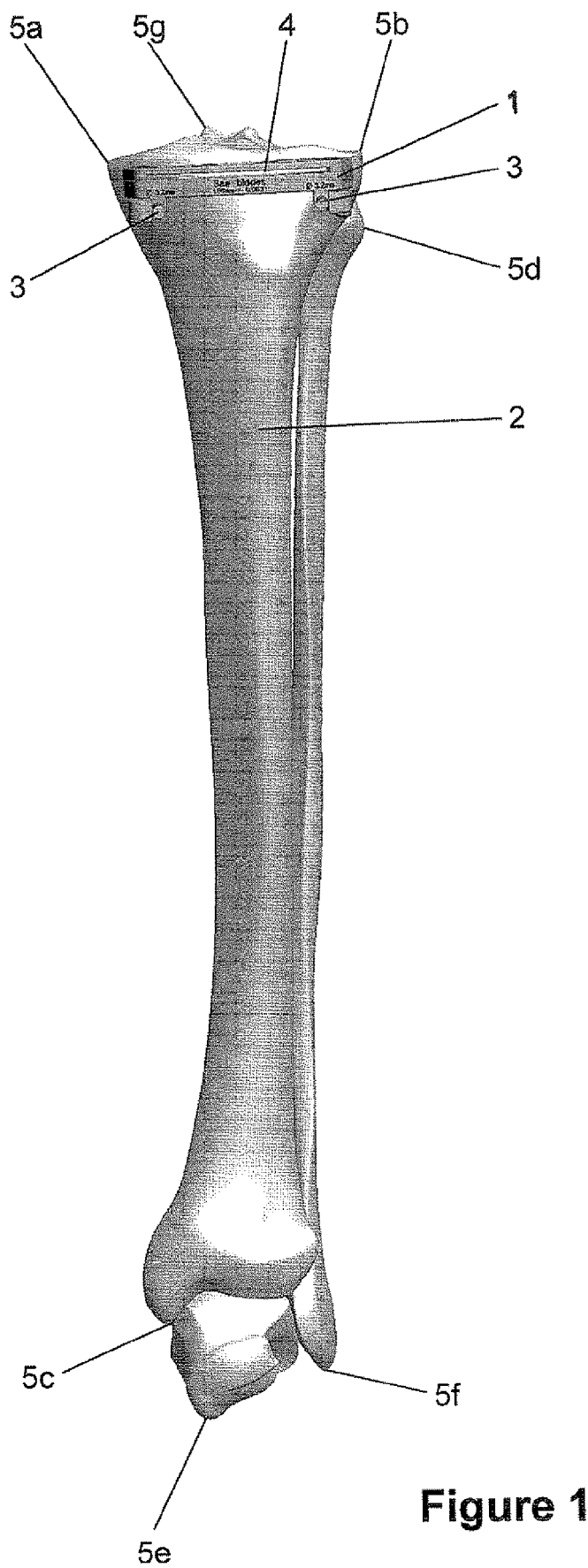
FIG. 1 a simple cutting block, fixed to a bone.

FIG. 1 shows a simple cutting block 1 as an example of a medical instrument which is rigidly affixed to a bone 2. In order to fix the cutting block 1 to the bone 2, two pins or Schanz screws 3 are fixed to the bone 2. The cutting block 1 is then attached to the pins 3 and thus rigidly affixed to the bone 2.

The cutting block 1 comprises a cutting slot 4 through which a saw blade (not shown) is guided in order to accurately excise a part of the bone 2, for example preparatory to installing an artificial joint. For this example application, and for many other applications, it is essential that the relative position between the cutting block 1, and therefore the cutting slot 4, and the bone 2 matches a desired relative position within an allowable tolerance.

FIG. 1 also shows points 5a to 5g on the surface of the bone 2. The locations of these points are represented by bone registration data, as explained below.

Figure 2:
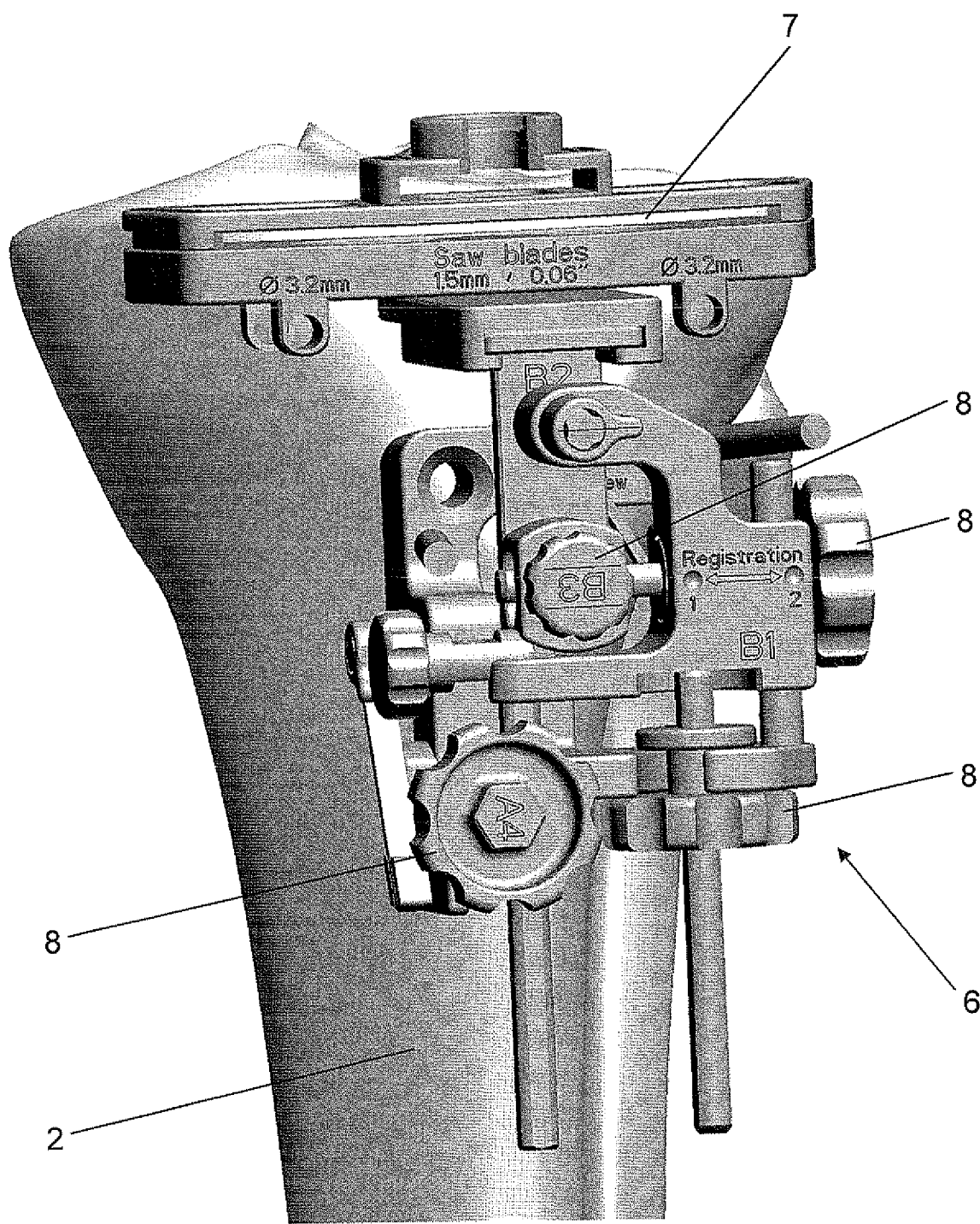
FIG. 2 an adjustable cutting block, fixed to a bone.

FIG. 2 shows an adjustable cutting block 6 as an alternative to the basic cutting block 1 of FIG. 1. The adjustable cutting block 6 comprises a base which is rigidly affixed to the bone 2 via pins, bolts or screws (not shown). The adjustable cutting block 6 comprises a cutting slot 7 which can be adjusted using setting screws 8. Using the setting screws 8, one or more of the following parameters can be adjusted: the slope, internal/external rotation, varus/valgus and resection height.

Figure 3:
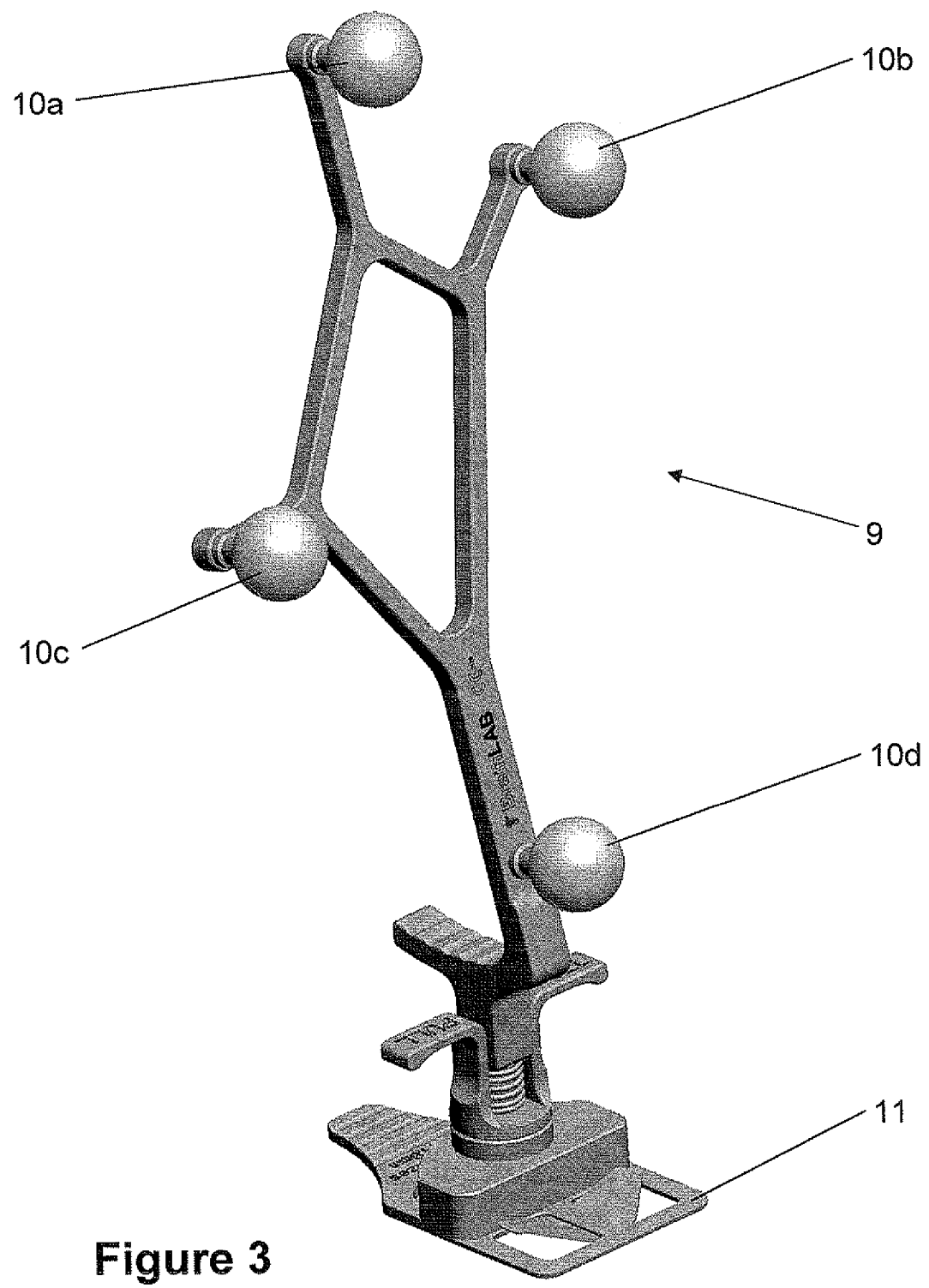
FIG. 3 a marker device.

FIG. 3 shows an example of a marker device 9 comprising a marker holder to which four marker spheres 10a to 10d are attached. Where the marker spheres do not need to be individually identified, they are referred to collectively as the marker spheres 10. The marker device 9 also comprises a plate or sheet 11 which is designed to fit into the cutting slot 4 or 7 of the cutting block 1 or 6, respectively. Via the plate or sheet 11, the marker device 9 can be temporarily affixed to the cutting block 1 or 6, respectively, in a rigid manner, i.e. such that no relative movement is possible between the cutting block 1 or 6, respectively, and the marker device 9.

Figure 4:
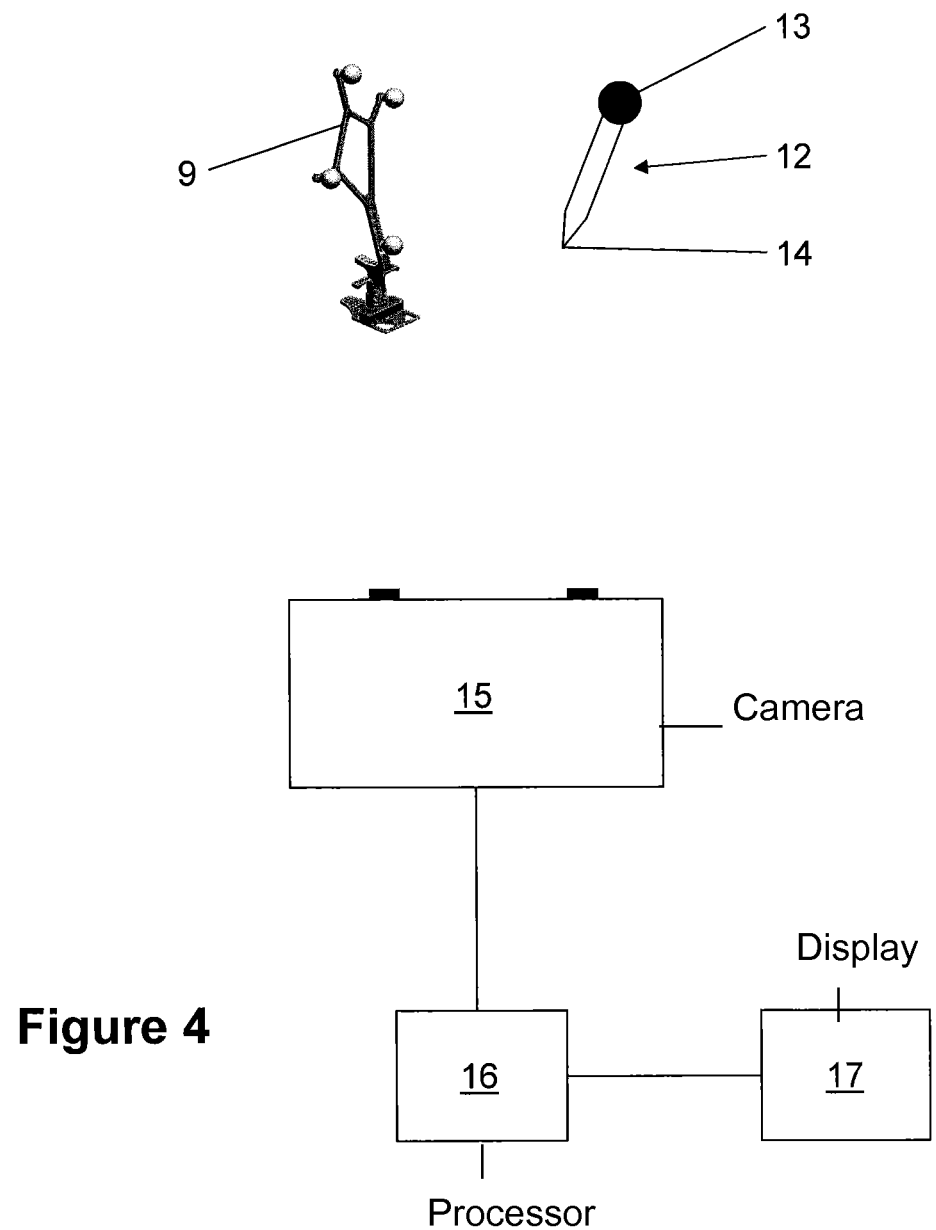
FIG. 4 a schematic diagram of a medical navigation system.

FIG. 4 schematically shows a medical navigation system comprising a stereoscopic camera 15 as a marker detection device, a central processing unit (CPU) 16 as a computer and a display 17 as an output device. The stereoscopic camera 15 also acts as a device for providing bone registration data and bone re-registration data.

FIG. 4 also shows the marker device 9 and a pointer 12. The pointer 12 comprises a marker device 13 at one end and a tip 14 at the other end. The stereoscopic camera 15 is configured to detect the positions of the marker devices 9 and 13. The position of the pointer 12, in particular the location of the tip 14 of the pointer 12, can be derived from the position of the marker device 13.

In order to perform the method according to the present invention, the marker device 9 is rigidly attached to the cutting block 1 or 6, respectively, by inserting the plate or sheet 11 into the cutting slot 4 or 7, respectively. The position of the cutting slot 4 or 7, respectively, can then be determined from the position of the marker device 9.

In a first step, the CPU 16 receives bone registration data which represent the locations of the points 5a to 5g on the surface of the bone 2. The bone registration data are provided by the stereoscopic camera 15, for example by sampling the points using the pointer 12. The tip 14 of the pointer 12 is held at the point to be sampled, and the stereoscopic camera 15 determines the location of the tip 14, and therefore the location of the point on the surface of the bone 2, from the position of the marker device 13 and the known positional relationship between the tip 14 and the marker device 13.

In a first preferred embodiment, the bone registration data are specified in a co-ordinate system which is linked to the stereoscopic camera 15. The stereoscopic camera 15 also then provides the position of the marker device 9 which is then received by the CPU 16. The position of the marker device 9 is represented by marker device position data. In a second preferred embodiment, the stereoscopic camera 15 provides the bone registration data in a coordinate system which is linked to the marker device 9. In this case, the locations of the sampled points 5a to 5g are specified relative to the marker device 9.

In a second step, the current relative position between the bone 2 and the cutting slot 4 or 7, respectively, is calculated from the bone registration data. The current relative position is represented by current relative position data. The position of the cutting slot 4 or 7, respectively, designates the cutting plane of a cut using a saw and the cutting block 1 or 6, respectively. An offset between the current relative position and a desired relative position of the cutting slot 4 or 7, respectively, is then calculated in a third step. This offset also represents the difference between a current cutting plane and a desired cutting plane.

In a fourth step, indication information which is based on the calculated offset is outputted using the display 17. If the offset is within a tolerable range, a corresponding signal is outputted by the display 17. Additionally or alternatively, the indication information can be absolute values which represent the offset. The indication information can optionally contain information on how the cutting block 1 or 6, respectively, has to be adjusted in order to achieve the desired relative position between the cutting slot 4 or 7, respectively, and the bone 2. The simple cutting block 1 can be adjusted by replacing the cutting block with another cutting block, the cutting slot of which is in a correct position relative to the pins 3 and therefore to the bone 2. Optionally, the CPU 16 has access to a database of simple cutting blocks, wherein different cutting blocks have different positions of the cutting slot within the cutting block, or a model of the adjustable cutting block which represents the effects of adjusting each setting screw of the adjustable cutting block.

When the cutting block is adjusted, the marker device 9 is moved relative to the bone 2, and the positional relationship between the bone 2 and the marker device 9 as calculated in the second step is therefore lost. In a fifth step, the stereoscopic camera 15 provides bone re-registration data which are received by the CPU 16. The bone re-registration data represent the locations of the points 5a to 5c on the surface of the bone 2. The bone re-registration data are a reduced set of data as compared to the bone registration data because they only contain the locations of three points rather than seven points as in the bone registration data. Since the bone 2 remains the same, the relative locations of the points 5a to 5g also remain the same. This means that the locations of the three points 5a to 5c are sufficient to determine the position of the bone 2, because the bone registration data can be transformed such that the points 5a to 5c in the bone registration data match the points 5a to 5c in the bone re-registration data. The transformed locations of the points 5d to 5g then match the current, actual locations of these points.

In a sixth step, the positional relationship which represents the position of the marker device 9 relative to the bone 2 is calculated from the bone re-registration data, in a similar way to the second step. Once this positional relationship has been re-established, there is then again a known and fixed relationship between the marker device 9 and the bone 2. The marker device 9 can therefore be used to navigate the bone 2 in the medical navigation system, without having to attach a dedicated marker device to the bone 2.

Instead of a cutting block, other medical instruments which are capable of bearing a marker device can be used to implement the method according to the present invention. Examples of other medical instruments include splints or implants.

Using the method according to the present invention, it is possible to use established medical instruments in medical navigation systems. Thus, the surgeon does not have to familiarise himself with new instruments.

As an alternative to the marker device 9, it is also possible to determine the position of the cutting slot 4 or 7, respectively, by sampling defined points on the surface of the cutting block 1 or 6, respectively, using the pointer 12. In this case, there is no marker device 9 present which could impede the adjustment of the cutting block 1 or 6, respectively. In one application, the tip 14 of the pointer 12 is held at a defined point on the surface of the bone 2 while the cutting block 1 or 6, respectively, is adjusted in one degree of freedom, for example the resection height of a tibial cut. In this application, the position of the cutting slot 4 or 7, respectively, can be tracked over time. Preferably, an information signal is outputted once the cutting slot 4 or 7, respectively, has reached a target position. If the bone 2 is immobilised relative to the stereoscopic camera 15, then the step of placing the tip 14 of the pointer 12 onto the point on the surface of the bone 2 can be omitted.

The location of a point on the surface of the bone 2 can be acquired using the pointer 12 and without any incision or other surgical step by placing the tip 14 of the pointer 12 onto a location on the skin, through which said point is apparent. In another example, the tip 14 of the pointer 12 can be placed directly onto the surface of the bone if the bone has been at least partly exposed in a previous step in which an incision was made but which is preferably not part of the present invention. The pointer can be placed onto the point on the surface of the bone by any member of staff, even one without medical expertise, in particular if the point to be sampled is indicated, and preferably shown on an image of the bone, on the display.

In another example, the location of a point on the surface of the bone can be acquired without touching the bone or the body comprising the bone, for example using non-invasive imaging methods such as x-ray, CT, MRT, MRI and the like. Optical imaging methods, such as 3D photography, can also be used, in particular if the bone is already exposed. The point and its location can then be detected from the image, either automatically or by user intervention.

Re-adjusting the cutting block does not require professional medical expertise because it is a simple operating step of the cutting block. This applies in particular if the cutting block is adjustable and the display shows how the setting screws of the cutting block have to manipulated, or if the cutting block is a simple cutting block and the display shows the cutting block with which the current cutting block has to be replaced. Replacing a simple cutting block does not require any interaction with the bone or the body itself, but only with the pins, screws or bolts which were previously implanted into the bone.

The invention claimed is:

1. A method for determining a position of a bone, the method comprising:
   receiving bone registration data into an associated computer, the bone registration data being representative of spatial locations of a first set of points which lie on a surface of a bone relative to an associated marker device carried by an associated adjustable cutting block affixed to the bone, wherein the associated adjustable cutting block defines a cutting slot and wherein the associated marker device is rigidly coupled with the cutting block by a plate of the marker device received in the cutting slot of the associated adjustable cutting block thereby establishing a fixed relative position between the associated marker device and the cutting slot of the associated adjustable cutting block;
   processing the bone registration data by the associated computer to calculate, based on the bone registration data and the fixed relative position between the associated marker device and the cutting slot of the cutting block, a current relative position between the bone and the cutting slot of the associated adjustable cutting block;
   determining, by the associated computer, an offset between:
      the current relative position between the cutting slot and the bone, and
      a desired relative position between the cutting slot and the bone;
   outputting indication information by the associated computer, wherein the indication information is provided for indicating an adjustment to be made to the associated adjustable cutting block based on the determined offset such that a relative movement between the cutting slot carrying the associated marker device and the bone is caused;
   receiving degree of freedom data into the associated computer, the degree of freedom data being representative of a number of degrees of freedom of movement of the bone;
   receiving, following the adjustment to the associated adjustable cutting block such that the relative movement between the cutting slot carrying the associated marker device and the bone is caused, bone re-registration data into the associated computer, the bone re-registration data being representative of spatial locations of one or more points forming a second set of points which lie on the surface of the bone, wherein a quantity of the one or more points forming the second set of points is based on the received number of degrees of freedom of movement of the bone and wherein the second set of points comprises fewer points than the first set of points; and
   tracking a position of the bone using a determined position of the associated marker device and the bone re-registration data.

2. The method according to claim 1, wherein the receiving the bone re-registration data comprises:
   receiving bone re-registration data representative of spatial locations of a number of points equal to or larger than the received number of degrees of freedom of movement forming the second set of points which lie on the surface of the bone.

3. The method according to claim 1, wherein:
   the receiving the degree of freedom data into the associated computer comprises receiving degree of freedom data representative of a single degree of freedom of movement of the bone; and
   the receiving the bone re-registration data into the associated computer comprises receiving bone re-registration data representative of a spatial location of a single point that lays on the surface of the bone.

4. The method according to claim 1, wherein the receiving the degree of freedom data into the associated computer comprises:
   receiving the degree of freedom data into the associated computer from a memory storage device of the associated computer.

5. The method according to claim 1, wherein the receiving the degree of freedom data into the associated computer comprises:
   receiving the degree of freedom data into the associated computer from an associated input device operatively coupled with the associated computer.

6. The method according to claim 5, wherein the receiving the degree of freedom data into the associated computer from the associated input device comprises:
   receiving the degree of freedom data into the associated computer from an associated keyboard or touch screen operatively coupled with the associated computer.

7. The method according to claim 1, wherein the receiving the bone registration data, the processing the bone registration data, the determining the offset, and the outputting the indication information are repeated until the offset is below a predetermined threshold.

8. A non-transitory computer readable medium storing a computer program that, when running on an associated computer or loaded onto the associated computer for execution by a processor of the associated computer, causes the associated computer to perform a method for determining a position of a bone comprising:
   receiving bone registration data into the associated computer, the bone registration data being representative of spatial locations of a first set of points which lie on a surface of a bone relative to an associated marker device carried by an associated adjustable cutting block affixed to the bone, wherein the associated adjustable cutting block defines a cutting slot and wherein the associated marker device is rigidly coupled with the cutting block by a plate of the marker device received in the cutting slot of the associated adjustable cutting block thereby establishing a fixed relative position between the associated marker device and the cutting slot of the associated adjustable cutting block;

processing the bone registration data by the associated computer to calculate, based on the bone registration data and the fixed relative position between the associated marker device and the cutting slot of the cutting block, a current relative position between the bone and the cutting slot of the associated adjustable cutting block;

determining, by the associated computer, an offset between:
- the current relative position between the cutting slot and the bone, and
- a desired relative position between the cutting slot and the bone;

outputting indication information by the associated computer, wherein the indication information is provided for indicating an adjustment to be made to the associated adjustable cutting block based on the determined offset such that a relative movement between the cutting slot carrying the associated market device and the bone is caused;

receiving degree of freedom data into the associated computer, the degree of freedom data being representative of a number of degrees of freedom of movement of the bone;

receiving, following the adjustment to the associated adjustable cutting block such that the relative movement between the cutting slot carrying the associated marker device and the bone is caused, bone re-registration data into the associated computer, the bone re-registration data being representative of spatial locations of one or more points forming a second set of points which lie on the surface of the bone, wherein a quantity of the one or more points forming the second set of points is based on the received number of degrees of freedom of movement of the bone and wherein the second set of points comprises fewer points than the first set of points; and tracking a position of the bone using a determined position of the associated marker device and the bone re-registration data.

9. The non-transitory computer readable medium according to claim 8, wherein the receiving the bone re-registration data comprises:
receiving bone re-registration data representative of spatial locations of a number of points equal to or larger than the received number of degrees of freedom of movement forming the second set of points which lie on the surface of the bone.

10. The non-transitory computer readable medium according to claim 8, wherein:
the receiving the degree of freedom data into the associated computer comprises receiving degree of freedom data representative of a degree of a single freedom of movement of the bone; and
the receiving the bone re-registration data into the associated computer comprises receiving bone re-registration data representative of a spatial location of a single point that lays on the surface of the bone.

11. The non-transitory computer readable medium according to claim 8, wherein the receiving the degree of freedom data into the associated computer comprises:
receiving the degree of freedom data into the associated computer from a memory storage device of the associated computer.

12. The non-transitory computer readable medium according to claim 8, wherein the receiving the degree of freedom data into the associated computer comprises:
receiving the degree of freedom data into the associated computer from an associated input device operatively coupled with the associated computer.

13. The non-transitory computer readable medium according to claim 12, wherein the receiving the degree of freedom data into the associated computer from the associated input device comprises:
receiving the degree of freedom data into the associated computer from an associated keyboard or touch screen operatively coupled with the associated computer.

14. The non-transitory computer readable medium according to claim 8, wherein the receiving the bone registration data, the processing the bone registration data, the determining the offset, and the outputting the indication information are repeated until the offset is below a predetermined threshold.

15. A system for determining a position of a bone, the system comprising:
a memory device storing a computer program;
a computer comprising a processor operable to execute the computer program stored in the memory device to:
receive bone registration data into the system, the bone registration data being representative of spatial locations of a first set of points which lie on a surface of a bone relative to an associated marker device carried by an associated adjustable cutting block affixed to the bone, wherein the associated adjustable cutting block defines a cutting slot and wherein the associated marker device is rigidly coupled with the cutting block by a plate of the marker device received in the cutting slot of the associated adjustable cutting block thereby establishing a fixed relative position between the associated marker device and the cutting slot of the associated adjustable cutting block;
process the bone registration data to calculate, based on the bone registration data and the fixed relative position between the associated marker device and the cutting slot of the cutting block, a current relative position between the bone and the cutting slot of the associated adjustable cutting block;
determine an offset between:
- the current relative position between the cutting slot and the bone, and
- a desired relative position between the cutting slot and the bone;

output indication information, wherein the indication information is provided for indicating an adjustment to be made to the associated adjustable cutting block based on the determined offset such that a relative movement between the cutting slot carrying the associated marker device and the bone is caused;

receive degree of freedom data into the system, the degree of freedom data being representative of a number of degrees of freedom of movement of the bone;

receive, following the adjustment to the associated adjustable cutting block such that the relative movement between the cutting slot carrying the associated marker device and the bone is caused, bone re-registration data into the system, the bone re-registration data being representative of spatial locations of one or more points forming a second set of points which lie on the surface of the bone, wherein a quantity of the one or more points forming the second set of points is based on the received number of degrees of freedom of movement of the bone and wherein the second set of points comprises fewer points than the first set of points; and track a position of the bone using a determined position of the associated marker device and the bone re-registration data.

16. The system according to claim 15, wherein the processor is operable to receive the bone re-registration data by:
receiving bone re-registration data representative of spatial locations of a number of points equal to or larger than the received number of degrees of freedom of movement forming the second set of points which lie on the surface of the bone.

17. The system according to claim 15, wherein:
the processor is operable to the receive the degree of freedom data by receiving degree of freedom data representative of a single degree of freedom of movement of the bone; and
the processor is operable to receive the bone re-registration data by receiving bone re-registration data representative of a spatial location of a single point that lays on the surface of the bone.

18. The system according to claim 15, wherein the processor is operable to receive the degree of freedom data by receiving the degree of freedom data from the memory device.

19. The system according to claim 15, wherein the processor is operable to receive the degree of freedom data by:
receiving the degree of freedom data from an associated input device operatively coupled with the system.

20. The system according to claim 19, further comprising:
a keyboard or touch screen operatively coupled with the computer, wherein the system is operable to receive the degree of freedom data by receiving the degree of freedom data via the keyboard or touch screen.

21. The system according to claim 15, wherein the processor is operable to
repeatedly receive the bone registration data, process the bone registration data, determine the offset, and output the indication information until the offset is below a predetermined threshold.

* * * * *